(12) United States Patent
Benoit et al.

(10) Patent No.: US 12,274,825 B2
(45) Date of Patent: Apr. 15, 2025

(54) RESCUE BREATHING DEVICE

(71) Applicant: University of Cincinnati, Cincinnati, OH (US)

(72) Inventors: Justin Benoit, Cincinnati, OH (US); Ephraim Gutmark, Cincinnati, OH (US); Jason Mcmullan, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 732 days.

(21) Appl. No.: 17/297,206

(22) PCT Filed: Dec. 6, 2019

(86) PCT No.: PCT/US2019/064843
§ 371 (c)(1),
(2) Date: May 26, 2021

(87) PCT Pub. No.: WO2020/118138
PCT Pub. Date: Jun. 11, 2020

(65) Prior Publication Data
US 2022/0023558 A1    Jan. 27, 2022

Related U.S. Application Data

(60) Provisional application No. 62/776,657, filed on Dec. 7, 2018.

(51) Int. Cl.
*A61M 16/06* (2006.01)
*A61M 16/00* (2006.01)

(52) U.S. Cl.
CPC .... *A61M 16/0084* (2014.02); *A61M 16/0078* (2013.01); *A61M 16/0093* (2014.02);
(Continued)

(58) Field of Classification Search
CPC .... A61H 2201/0103; A61H 2201/0207; A61H 2201/0214; A61H 2201/025;
(Continued)

(56) References Cited

U.S. PATENT DOCUMENTS 4,397,306 A * 8/1983 Weisfeldt .......... A61M 16/0051
                                                          601/41
4,863,385 A * 9/1989 Pierce .................. G09B 23/288
                                                          601/41
(Continued)

FOREIGN PATENT DOCUMENTS

CA    2610334 A1    5/2008
EP    2707068 A1    3/2014
(Continued)

OTHER PUBLICATIONS

International Search Report and Written opinion dated Jan. 31, 2020 pertaining to PCT Application No. PCT/US2019/064843 filed Dec. 6, 2019.
(Continued)

*Primary Examiner* — Annette Dixon
(74) *Attorney, Agent, or Firm* — Dinsmore & Shohl LLP

(57) ABSTRACT

A ventilation system for ventilation of a patient includes a patient interface device for attaching to the patient and a measuring and analysis device for measuring and analyzing breathing of the patient. The measuring and analysis device includes a connector housing defining a passage. A first portion of the connector housing is connected to the patient interface device. The measuring and analysis device further includes an air flow sensor and a pressure sensor disposed in the connector housing for measuring an air flow rate through the connector housing and a pressure in the connector housing respectively. The present device also includes a processor configured for data acquisition, data storage, data processing, and data output based on the air flow rate and the
(Continued)

pressure, whereby the ventilation system is operable with real-time feedback based on the data output. A method for administering cardiopulmonary resuscitation is also provided.

25 Claims, 5 Drawing Sheets

(52) U.S. Cl.
CPC .......... *A61M 16/024* (2017.08); *A61M 16/06* (2013.01); *A61M 2016/0027* (2013.01); *A61M 2016/0036* (2013.01); *A61M 2205/05* (2013.01); *A61M 2205/3334* (2013.01); *A61M 2205/502* (2013.01); *A61M 2205/581* (2013.01); *A61M 2205/582* (2013.01); *A61M 2205/583* (2013.01); *A61M 2205/75* (2013.01); *A61M 2230/42* (2013.01); *A61M 2230/432* (2013.01)

(58) Field of Classification Search
CPC .... A61H 2201/0257; A61H 2201/0285; A61H 2201/10; A61H 2201/105; A61H 2201/107; A61H 2201/1238; A61H 2201/165; A61H 2201/5007; A61H 2201/501; A61H 2201/5043; A61H 2201/5048; A61H 2201/5058; A61H 2201/5061; A61H 2201/5064; A61H 2201/5089; A61H 2201/5097; A61H 2205/083; A61H 2230/00; A61H 2230/04; A61H 2230/045; A61H 2230/08; A61H 2230/205; A61H 2230/207; A61H 2230/50; A61H 31/00; A61H 31/004; A61H 31/005; A61H 31/006; A61H 31/008; A61H 9/0078; A61M 15/02; A61M 16/00; A61M 16/0003; A61M 16/0009; A61M 16/0051; A61M 16/0057; A61M 16/0063; A61M 16/0066; A61M 16/0069; A61M 16/0072; A61M 16/021; A61M 16/022; A61M 16/024; A61M 16/0465; A61M 16/06; A61M 16/10; A61M 16/101; A61M 16/107; A61M 16/1075; A61M 16/108; A61M 16/12; A61M 16/20; A61M 16/202; A61M 16/204; A61M 16/209; A61M 2016/0021; A61M 2016/0027; A61M 2016/0033; A61M 2016/0036; A61M 2016/0039; A61M 2016/1025; A61M 2016/1035; A61M 2202/0208; A61M 2202/0216; A61M 2202/0275; A61M 2205/04; A61M 2205/33; A61M 2205/3303; A61M 2205/332; A61M 2205/3334; A61M 2205/3344; A61M 2205/3355; A61M 2205/3358; A61M 2205/3553; A61M 2205/3561; A61M 2205/3569; A61M 2205/3584; A61M 2205/3592; A61M 2205/3606; A61M 2205/366; A61M 2205/50; A61M 2205/505; A61M 2205/52; A61M 2205/581; A61M 2205/583; A61M 2205/7545; A61M 2210/1032; A61M 2230/04; A61M 2230/10; A61M 2230/18; A61M 2230/202; A61M 2230/30; A61M 2230/40; A61M 2230/432; A61M 2230/435; A61M 2230/50; A61M 2230/60; A61M 2230/63; A61N 1/39044; A61N 1/3987; B01D 2251/304; B01D 2251/306; B01D 2251/404; B01D 53/56; C01B 21/203; F04D 25/166; F04D 29/052; F04D 29/286; G09B 23/288; Y02A 50/20; Y10S 601/08
See application file for complete search history.

(56) References Cited

U.S. PATENT DOCUMENTS

| | | | |
|---|---|---|---|
| 5,327,887 A * | 7/1994 | Nowakowski | A61M 16/024 128/202.13 |
| 5,503,146 A * | 4/1996 | Froehlich | A61M 16/0069 128/204.23 |
| 6,155,257 A * | 12/2000 | Lurie | A61H 31/006 128/205.24 |
| 6,349,724 B1* | 2/2002 | Burton | F04D 29/052 128/204.22 |
| 8,567,398 B2* | 10/2013 | Truschel | A61M 16/0069 128/204.23 |
| 2003/0105407 A1 | 6/2003 | Pearce, Jr. et al. | |
| 2007/0225623 A1* | 9/2007 | Freeman | A61N 1/39044 601/44 |
| 2007/0261698 A1 | 11/2007 | Palatnik | |
| 2008/0092898 A1 | 4/2008 | Schneider et al. | |
| 2012/0016179 A1* | 1/2012 | Paradis | A61N 1/3987 601/41 |
| 2015/0096559 A1 | 4/2015 | Duval-Arnould et al. | |
| 2015/0238722 A1 | 8/2015 | Al-Ali | |
| 2015/0283342 A1 | 10/2015 | Mielcarz et al. | |
| 2016/0038710 A1* | 2/2016 | Zapol | A61M 16/20 128/202.26 |
| 2017/0266399 A1 | 9/2017 | Campana et al. | |
| 2018/0160970 A1 | 6/2018 | Polycaptil et al. | |
| 2018/0272004 A1 | 9/2018 | DeRosa et al. | |

FOREIGN PATENT DOCUMENTS

| | | |
|---|---|---|
| JP | 2018521712 A | 8/2018 |
| WO | 2012162048 A1 | 11/2012 |
| WO | 2016198275 A1 | 12/2016 |
| WO | 2018083634 A1 | 11/2018 |

OTHER PUBLICATIONS

JP Notice of Reasons for Rejection dated Aug. 29, 2023 pertaining to JP application No. 2021-532185 filed Jun. 7, 2021, pp. 1-5.
Communication pursuant to Article 94(3) EPC dated May 3, 2023 pertaining to EP application No. 19893370.7 filed Jun. 9, 2021, pp. 1-6.
Losert, MD, H. et al. "Thoracic impedance changes measured via defibrillator pads can monitor ventilation in critically ill patients and during cardiopulmonary resuscitation" Critical Care Medicine, Lippincott Williams & Wilkins, 2006, pp. 2399-2405, vol. 34, No. 9.
JP Notice of Reasons for Rejection dated Dec. 11, 2023 pertaining to JP application No. 2021-532185 filed Jun. 7, 2021, pp. 1-6.
Extended European Search Report dated Jul. 29, 2022 pertaining to EP application No. 19893370.7 filed Jun. 9, 2021, pp. 1-11.
Khoury, et al., "Ventilation feedback device for manual ventilation in simulated respiratory arrest: a crossover manikin study", Scandinavian Journal of Trauma, Resuscitation Emergency Medicine, vol. 27, No. 93, pp. 1-8, 2019.
Hayes, et al., "Nebulizer Mask", Advantages and Disadvantages, pp. 1-3, Oct. 2022. https://url.us.m.mimecastprotect.com/s/ITdUCBBnGMTjo7jBhzflH2nPrv?domain=verywellhealth.com.

* cited by examiner

RESCUE BREATHING DEVICE

CROSS-REFERENCE TO RELATED APPLICATIONS

This application is a § 371 National Stage Entry of International Application No. PCT/US2019/064843, filed Dec. 6, 2019, which claims priority to U.S. Provisional Application Ser. No. 62/776,657, filed Dec. 7, 2018, each of which is incorporated by reference herein in its entirety.

TECHNICAL FIELD

The present disclosure relates to a device for measuring and providing feedback and analysis on ventilation provided to a person requiring assisted breathing or spontaneous breathing.

BACKGROUND

Cardiac arrest is a critical illness of whole-body organ damage resulting from the sudden cessation of heart and lung function. Cardiac arrest is a major public health crisis, affecting 400,000 adults and children outside the hospital each year in the United States. An additional 200,000 patients have in-hospital cardiac arrest each year. Without intervention, permanent organ damage and death occurs within minutes. Only 10% of patients who suffer cardiac arrest will survive.

Cardiopulmonary resuscitation (CPR) has been the cornerstone of treatment for cardiac arrest since first described in the 1950s. CPR involves compressing the chest wall to circulate the blood and delivering breaths of oxygen to ventilate the lungs. CPR can reverse critical organ damage, helping to restart the heart and lungs, and improve survival from cardiac arrest.

Improper ventilation can impair blood flow to the brain and heart muscle itself, damage the lungs, and worsen the critical acid-base balance of the blood. However, no device exists to measure how best to breathe for a patient.

No technology currently exists that can differentiate airflow due to rescue breaths from inadvertent airflow caused by physical compression of the thoracic cavity. No technology currently exists that is capable of assessing the synchronization between chest compressions and rescue breaths.

American Heart Association Cardiac Arrest Guidelines recommend rescue breaths be delivered at a rate of 8 to 10 per minute, with each breath delivered over 1 second, and a tidal volume that produces minimal chest rise. These recommendations are based on expert opinion only, and have not changed since cardiopulmonary resuscitation was first described in the 1970s. No technology currently exists that can reliably measure and report any of these ventilation parameters.

The bag valve mask, abbreviated BVM, is a device commonly used to provide breathing assistance to patients in situations of respiratory failure or respiratory arrest. The components of a standard BVM include a mask, a one-way valve to prevent backflow, and a flexible air bag. By squeezing the bag, the air flows into the patient's airway through the mask. However, poor technique is common, resulting in ineffective rescue breaths due to improper rate/depth/pressure, air leak around the mask and gastric insufflation (air going into the stomach instead of the lungs). Physical exam techniques to identify inadequate mask seal and lung ventilation are challenging to perform during clinical care, and no technology currently exists to provide real-time feedback.

There is an urgent clinical need to measure and control breathing for patients in cardiac arrest, in cardiac failure, or with respiratory insufficiency.

SUMMARY

Accordingly, provided herein are embodiments of a measuring and analysis device for measuring and analyzing breathing for a patient.

In an embodiment, the measuring and analysis device includes a connector housing defining a passage, an air flow sensor disposed in the connector housing for measuring an air flow rate through the connector housing in both directions, and a pressure sensor disposed in the connector housing for measuring a pressure in the connector housing in both directions.

The measuring and analysis device may further include a computer processor for data acquisition, data storage, data processing and data output, and a digital display attached to the computer processor for displaying the data output and providing real-time feedback. Other types of data output can also be used, such as light, sound, and/or tactile feedback.

The measuring and analysis device may be integrated into a ventilation system for ventilation of a patient. The measuring and analysis device can be a plug-and-play connection to a ventilation system, fitting between a patient interface device and a ventilation device, which can be quickly attached or detached. The ventilation system may include a patient interface device for attaching to the patient, such as a face mask or endotracheal tube or supraglottic airway. A first portion of the connector housing of the measuring and analysis device is connected to the patient interface device. The ventilation system may be an assisted ventilation system further comprising a ventilation device for delivering ventilation to the patient. A second portion of the connector housing is connected to the ventilation device. The measuring and analysis device enables the ventilation system to be operable in a controlled manner with real-time feedback based on the air flow rate and pressure.

The measuring and analysis device may also be used in a spontaneously breathing patient where the measuring and analysis device is connected to a patient interface device and configured to measure the breathing of the patient, thereby providing the respiratory parameter as output.

The measuring and analysis device may also be used in a mouth-to-mask system. The rescue breaths and the patient's breathing can both be measured.

In one embodiment, the measuring and analysis device is clean/sterile and disposable, including the sensor, processor, and display/output components. Such disposable embodiments are suitable for a single patient use. In embodiments, the measuring and analysis device is pre-assembled and may be ready to use at a moment's notice, which is ideal for military and other wilderness/rural applications where weight is an important consideration and the ability to easily replace a damaged unit is valued. In embodiments, the device would also be useful for crash/code carts in medical facilities that rarely see critically ill patients, such as dialysis centers, outpatient surgery centers, outpatient medical offices, and dentist offices. In some embodiments, the device can be a simple autonomous system that can be used at home or in public places, such as in a defibrillator.

In another embodiment, the measuring and analysis device is reusable, including the sensor, processor, and display/output components, and can be cleaned/sterilized for repeated use. Embodiments comprising a reusable measuring and analysis device would be useful for training scenarios where mannequins are used to train clinical staff on the use of present device and the use of self-inflating bags to provide rescue breaths to critically ill patients.

In another embodiment, certain components of the measuring and analysis device are clean/sterile and disposable, packaged separately, and suitable for single patient use, while other components are reusable. For example, the sensor component may be disposable, while the processor and the display/output components are reusable. The processor and the display/output components may be integrated into another monitor/device, such as a cardiac monitor. Such embodiments would be ideal for heavy users of present device, such as an urban EMS agency, where they want to reduce costs of using the present device by having reusable components, but do not have the resources to clean/sterilize the entire device between patient encounters.

In one example, the device for delivering ventilation to the patient is a bag valve mask for performing cardiopulmonary resuscitation (CPR). The bag valve mask includes a flexible self-inflating bag, a one-way valve, and a mask. The measuring and analysis device is compact and fits in between the bag and the mask, with little change to the overall size of the bag valve mask.

The air flow sensor and the pressure sensor may be bidirectional. The air flow sensor and the pressure sensor may be built into an inline device. The air flow sensor may be a thermal, fluidic, acoustical, or optical flow sensor.

The response time of the pressure sensor may be at least 1 ms or less, enabling a sampling frequency of 500 Hz or above.

The ventilation system may further comprise an inline individual/combined medication administration and suction port on the patient side of the device, and a monitoring port for end-tidal $CO_2$ on the bag side of the device.

The ventilation system may further comprise a filter (such as sieve/screen/foam) or trap for filtering respiratory secretions (such as blood, saliva, or vomitus) over the air flow sensor and the pressure sensor.

In one embodiment, the measuring and analysis device of the present invention is self-contained. The sensor, processor, and display/output components are provided as a single medical device. The single medical device is pre-assembled and ready to use at a moment's notice. Such an embodiment would be ideal for military and other wilderness/rural applications where a cardiac monitors and other large medical devices are not feasible. Such an embodiment would also be useful for medical facilities that rarely see critically ill patients and want to add a single piece of equipment.

In another embodiment, the present device is configured into two separate pieces, with the processor and display/output components integrated into another monitor/device, such as a cardiac monitor, while the sensor component attaches independently to the bag-valve mask. Wireless or wired communication enables the sensor to relay information to the processor. Such an embodiment would be ideal for heavy users of the present device, such as an urban EMS agency or hospital system, who regularly purchase large patient monitoring devices that collect and display multiple patient vital signs simultaneously.

Based on the air flow rate and pressure, a number of respiratory parameters can be determined and evaluated. Respiratory parameters include, but are not limited to, baseline pressure, delivered and exhaled pressures, tidal volumes (milliliters per breath) and exhalation volumes (milliliters per breath), respiratory rates (breaths per minute), minute ventilation (liters per minute), chest compression rates (compressions per minute), chest compression depths, and chest compression fractions (time performing chest compressions divided by the total time).

In one embodiment, the present device can be configured to provide a full analysis and display of rescue breaths, chest compressions, and/or mask seal for advanced clinicians. Exemplary variables analyzed and displayed include, but are not limited to, respiratory rate, tidal volume, minute ventilation, volume exhaled, percentage of mask seal (volume exhaled divided by tidal volume), peak pressure (highest pressure during a breath), positive-end expiratory pressure (pressure between breaths), graphs of pressure and volume over time including pressure-volume loops, chest compression rate, CPR fraction, and the synchronization of chest compressions to rescue breaths, among others. Such an embodiment would be particularly useful for emergency physicians or intensive care physicians who have advanced training on pulmonary pathophysiology and cardiac arrest.

In another embodiment, the present device is configured to provide a focused analysis and display of information that is most needed during the initial resuscitation of critically ill patients and can be interpreted by a range of clinical providers. Variables analyzed and displayed would include respiratory rate, tidal volume, percentage of mask seal, and compression rate. Output can also include light, sound, and tactile feedback based on the adherence of reported variables to clinical guidelines. For example, if the respiratory rate and tidal volume meet American Heart Association guidelines for Advanced Cardiac Life Support, a green light will be visible on the measuring and analysis device. Such an embodiment would be particularly useful for clinical providers who must be certified in Advanced Cardiac Life Support, such as paramedics or nurses, and any clinical provider who needs to provide medical care in a chaotic environment.

In a another embodiment, the present device can be configured to provide minimal analysis and output on only the most critical patient variables, such as minute ventilation. For example, output of light, sound, and tactile feedback tells the clinical provider if there is a need to speed up or slow down their rescue breaths. Such an embodiment would be ideal for clinical providers who are not certified in Advanced Cardiac Life Support, such as emergency medical technicians, or any clinical providers who rarely treats critically ill patients, such as those who work in dialysis centers, outpatient surgery centers, outpatient medical offices, and dentist offices.

In yet another embodiment, only raw data is provided. The present device can be configured to provide a full analysis of all clinical data, but not display any information to the clinical provider. Instead, this information, along with the raw electrical data from the sensor component of the present device, is stored in the device for wireless or wired transmission/download to a computer. Such an embodiment would be ideal for research and training purposes, where blinding of the clinical provider is desired, and exploratory analysis may be completed at a later date.

The computer processor may be configured to include a storage medium for storing algorithms including sub routines for data acquisition, data analysis, and output processing. The computer may be adapted to report respiratory wave forms such as scalar waveforms (pressure, volume, and/or flow over time) and pressure-volume loops (pressure versus volume for any given inspiration and/or expiration cycle) and/or to provide real-time feedback on how to optimize ventilation based on these wave forms. The computer processor may also be adapted to provide a prescribed desired flow-time or pressure-time function that the operator can follow for optimal controlled provision of air. Such real-time feedback may include, for example, acoustic (e.g. pitches, verbal instructions) and/or light indicators.

In embodiments providing full or focused analysis, the computer processor may be configured to include a storage medium for storing a triple-threaded algorithm or more complex algorithm including sub routines for data acquisition, data analysis, output processing and graph plotting.

The computer processor may be adapted to store and time-stamp events for post-event analysis.

The measuring and analysis device may further comprise wireless communication devices such as Bluetooth for wireless communication with other devices.

In one embodiment, the measuring and analysis device is operable to differentiate rescue breaths from chest compressions. Since the breathing cycle and the cardiac cycle are at significantly different frequencies, they can be separated by filtering techniques, such as band pass filtering, Fast Fourier Transforms, phase averaging, wavelet analysis, and the like, to separate between the frequencies and amplitudes related to the rescue breaths and the chest compressions and determine the phase between them. Exemplary frequencies include, but are not limited to, a mean of about 10 and in the range of about 0-60 for rescue breaths and a mean of about 100 and in the range of about 60-160 for chest compressions.

The filtering techniques listed above also identify the phase relationship between the breath and chest compressions, their frequencies, and amplitudes. The measuring and analysis device may be operable to enable synchronization between the rescue breaths and the chest compressions by optimizing the timing, depth and/or duration of the rescue breaths to ensure the rescue breaths are delivered in a coordinated manner, regardless of whether an interrupted or continuous chest compression technique is used. The optimization relies on controlling frequencies, amplitudes, and the ability to synchronize the two via controlling the phase relationship between the two.

The measuring and analysis device may be operable to determine a seal quality of the mouthpiece and determination of airway blockage resulting in resistance to ventilation and determination of other abnormalities of rescue breathing based on the baseline pressure, delivered and exhaled pressures, delivery volumes, and exhalation volumes. Other abnormalities of rescue breathing may be pneumothorax or gastric insufflation.

In embodiments, the measuring and analysis device is operable to determine a quality of chest compressions and a quality of rescue breathing based on one or more parameters selected from chest compression rates, depths, amplitude, timing relative to breathing, fractions, baseline pressure, delivered and exhaled pressures, delivery volumes, exhalation volumes, respiratory rates, and minute ventilation.

The physiologic data collected by the present device intra-arrest, including respiratory rate (breaths per minute), tidal volume (milliliters per breath), minute ventilation (liters per minute), volume exhaled (milliliters per breath), peak pressure (highest pressure during a breath), positive-end expiratory pressure (pressure between breaths), and graphs of pressure and volume over time including pressure-volume loops, among others, can be used to inform and optimize ongoing ventilation in the post-arrest period such as informing initial settings for a mechanical ventilator. The applied parameters can be adapted to the age, gender, health condition of the specific patient.

Also provided herein is a method of administering cardiopulmonary resuscitation (CPR) with controlled rescue breaths. In embodiments, the method includes the steps of providing a bag valve mask including a measuring and analysis device as disclosed herein, measuring the air flow rate and the pressure, and evaluating one or more respiratory parameters based on the air flow rate and the pressure, the respiratory parameters being selected from a group including baseline pressure, peak pressure, tidal volume, and exhalation volume, respiratory rates, minute ventilation, chest compression rates, chest compression depths, and chest compression fractions.

In embodiments, the present method further includes differentiating rescue breaths from chest compressions using a signal filtering technique to detect a frequency and amplitude of changes in the air flow rate and pressure, and synchronizing the rescue breaths and the chest compressions by optimizing the timing, depth, and duration of the rescue breaths to ensure the rescue breaths are delivered in a manner that maximizes heart and lung function, regardless of whether an interrupted or continuous chest compression technique is used, whereby rescue breaths are delivered based on the real-time feedback and air delivered from chest compressions are distinguished from and synchronized with air from the rescue breaths during the performing of the CPR.

DETAILED DESCRIPTION

Provided herein are embodiments of a measuring and analysis device for measuring and analyzing breathing of a patient. The embodiments of the measuring and analysis device of the present invention have different configurations that meet the specific requirements of different end-users. The present device is used in situations where patients are critically ill, so these configurations have important implications on the ability of clinical staff to provide optimal medical care in a rapid time frame, including situations where resources are limited such as the prehospital/EMS environment. The present device can be used for any clinical scenario where ventilations are assisted by a rescuer. The present device can also be used to measure and monitor breathing in a spontaneously breathing patient.

Measuring and Analysis Device

Figure 1:
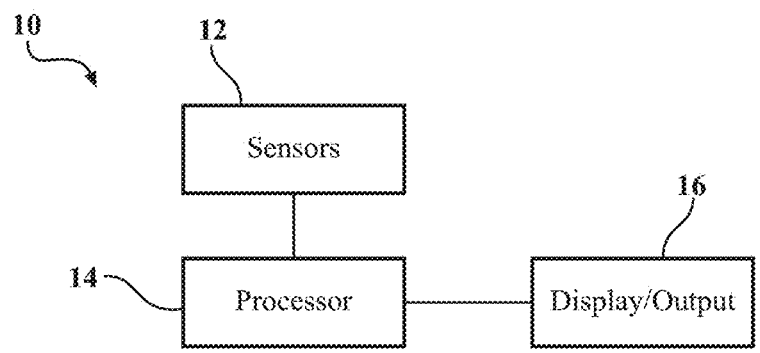
FIG. 1 is a schematic diagram of a measuring and analysis system in accordance with an embodiment of the present invention.

In one embodiment, as shown in FIG. 1, the measuring and analysis device 10 has three components, i.e., the sensors 12, processor 14, and display/output 16. The sensors may be housed in a sensor housing. In one example, the sensors 12 include an air flow sensor for measuring both inspiratory and expiratory air flow rate and a pressure sensor for measuring the pressure of the sensor housing. The air flow sensor and pressure sensor may be bi-directional.

Figure 2:
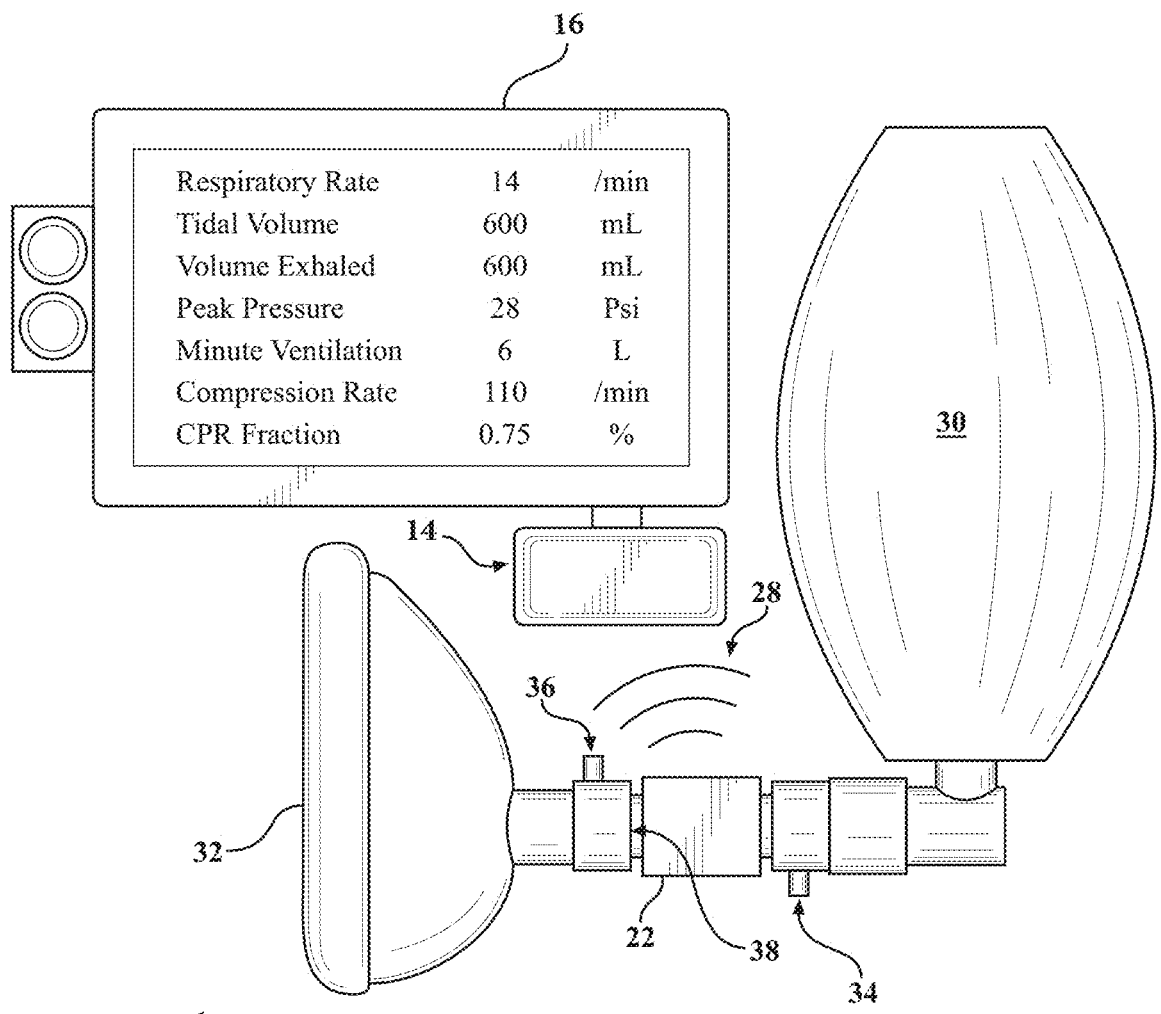
FIG. 2 is a schematic diagram of a measuring and analysis system in accordance with an embodiment of the present invention attached to a bag valve mask.

FIG. 2 shows a rescue breathing device 20 including a sensor device 22 used with a bag valve mask. The rescue breathing device 20 in FIG. 2 includes a self-inflating bag 30, a face mask 32. In some versions, the rescue breathing device 20 may only include a face mask 32 and a sensor device 22. The self-inflating bag 30 and face mask 32 can be separate or built-in. The face mask 32 is only one example of how the sensor device 22 connects to the patient. The face mask 32 can also be an alternative patient interface device such as supraglottic airway, endotracheal tube, or tracheostomy.

In an example, the rescue breathing device 20 contains a sensor device 22 including a flow meter and a pressure meter housed within a sensor housing. The flow and pressure meters are not visible in FIG. 2 and are described in detail hereinbelow. The flow and pressure meters may be bidirectional. The sensor device 22 is connected at one end to the face mask 32 and at the other end to the self-inflating bag 30 via universal connectors.

The rescue breathing device 20 further includes a processor 14 for data acquisition, data storage, data processing, and data output. For example, the processor 14 may be configured to receive the data from the flow and pressure meters. The processor 14 can connect to a display/output 16, such as a screen, and may be configured to export data to the display or an output. The output may include lights, sounds, or tactile feedback. The processor 14 may be stand-alone or integrated into an existing monitor. The display/output 16 can be physically attached to the processor 14 or integrated with the processor 14. The processor and display/output in FIG. 2 are not to scale and are enlarged views.

The processor 14 may be wired to the sensor device 22 or communicate to the sensor device 22 via a wireless connection 28.

The sensor device 22 may include ports for end-tidal $CO_2$ monitoring 34 and for medication and suction 36. The sensor device 22 may further include a filter 38 which blocks flow of respiratory secretions.

Figure 3:
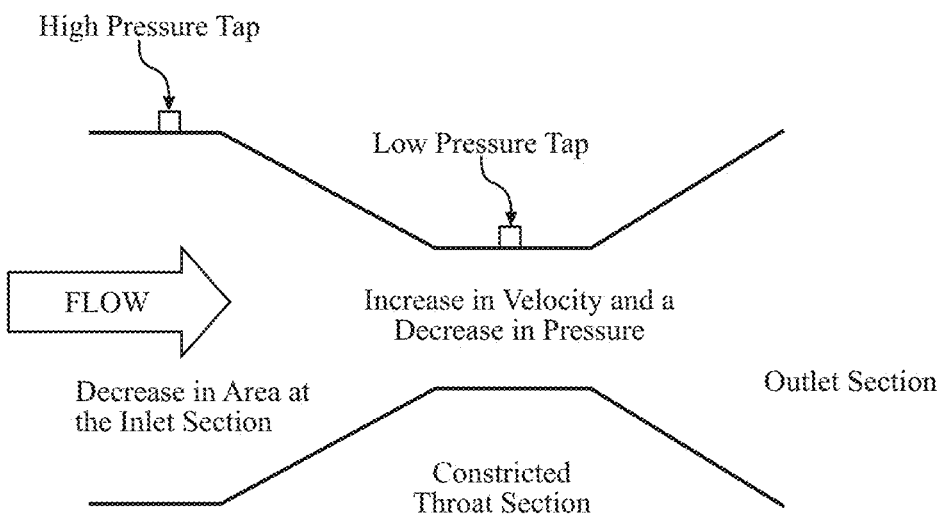
FIG. 3 is a schematic diagram showing an example of a connector housing of a measuring and analysis system in accordance with an embodiment of the present invention.

The air flow meter may be a compact flow meter. In one example, a flow meter uses the difference in pressure measured between high and low pressure taps to calculate flow rate, volume, and pressure, as shown in FIG. 3. Another pressure sensor may be added on the other side of the neck region to sense the direction of the flow.

In another example, a two-in-one, bi-directional air flow meter and pressure sensor designed for integrated solutions of mechanical respiration applications, such as the model FS6122 by Siargo Ltd., is chosen. The mass flow sensor is a thermal flow sensor which uses a temperature gradient across a small heater to measure changes in mass flow in either direction. A thermal mass flow sensor is able to accurately measure unsteady, bi-directional flow at the very low flow rates present when performing manual ventilation. In embodiments, the pressure sensor built into the FS6122 is a micro-electro-mechanical (MEMS) differential sensor that measures gauge pressure from the middle of the device. The pressure sensor is temperature compensated to handle a range of flow temperatures. The output of both sensors is analog voltage.

The sensor device 22 is compact and fits in between the bag and the mask with little overall change to the system size. Due to the nature of the sensors within the device, measurements can be taken with the device in any orientation relative to the patient, which is important when considering the clinical application. In embodiments, the response time of the full measurement unit is five milliseconds or less, for example, two milliseconds. The output of both sensors is analog voltage, which is sent to a compact data acquisition, processing, and display device. The voltage signals received by the compact data acquisitions device are scaled using calibrated maps to produce gauge pressure and mass flow signals. Rising and falling triggers are used to segment the signals into inspiratory and expiratory breaths. The individual breaths are integrated over their duration to produce volume based performance figures. The signals are also analyzed using fast Fourier transform to determine their respective frequencies and to be able to separate chest compressions from rescue breaths. The data acquisition system displays key variables in real time, as well as producing real time data analysis in order to guide the user in appropriate rescue breathing.

The model FS6122 sensor has a response time of about 5 ms or less, or more specifically about 2 ms, enabling a sampling frequency up to about 500 Hz, which exceeds the Nyquist criterion for adequately capturing the respiratory behavior of interest. A response time of 1 ms would allow a frequency of 1000 Hz. In this example, the mass flow sensor and the pressure sensor are both built into one compact and inline device. In a specific example, the integrated sensor measures about 67 mm×47 mm×31 mm. The compact configuration makes the addition of this device into a bag valve mask assembly far less intrusive and easier to handle than a bulkier measurement system. Furthermore, the model FS6122 sensor has a low power consumption. This is important in the situations where resources are limited such as the prehospital/EMS environment.

As shown in FIG. 1, the processor 14 is connected to the sensors 12 for data acquisition, data storage, data processing, and data output. In one embodiment, a microcomputer, such as Raspberry Pi, is selected to acquire voltage data from the flowmeter and to calculate the desired metrics from this voltage data. Raspberry Pi acts essentially as a mini version of a personal computer with a desktop and applications through which the code can run. Such an embodiment is suitable for certain applications that require a more robust operating system and require users' interaction with the program.

In one example, an SD card (for example, a 32 GB or higher SD card) is used as the main storage device. Raspbian, the operating system of the Raspberry Pi foundation, is the operating system chosen for the Raspberry Pi. As the Raspberry Pi has no analog input port, an analog-to-digital converter setup is needed in order to allow the use of the analog voltage signal coming from the mass-flow meter. To accomplish this, a DAQC2 plate is installed on top of the Raspberry Pi. The DAQC2 is a 16-bit data acquisition and control board capable of taking in eight analog inputs and converting them to digital signals. One function provided by the DAQC2 is plug-and-play capability with the Raspberry Pi and small form factor. In embodiments, the screen selected to output the data is also a Raspberry Pi-ready accessory that simply requires installation and the correct drivers to function. In embodiments, the screen is an LCF touchscreen, such as a 5" LCD touchscreen by Waveshare. As the measuring and analysis device is to be mobile, it must carry its own power supply. A rechargeable battery cell is suitable for use in powering the full system. A battery cell is optionally selected based on its compact size. A suitable rechargeable battery cell includes, for example, the Anker A1263. The Anker A1263 manufacturer indicates a capacity of 36 Wh, which allows for running for roughly 5.7 hours before the battery needs to be recharged.

In another embodiment, the processor is an Arduino processor. Three different Arduino boards, the Micro, the Uno, and the Mega, are selected. A larger screen is selected to go on either the Mega or Uno, and a smaller screen is selected to go on the micro. Other types of processors or displays suitable for the presently described purposes can also be used.

Figure 6:
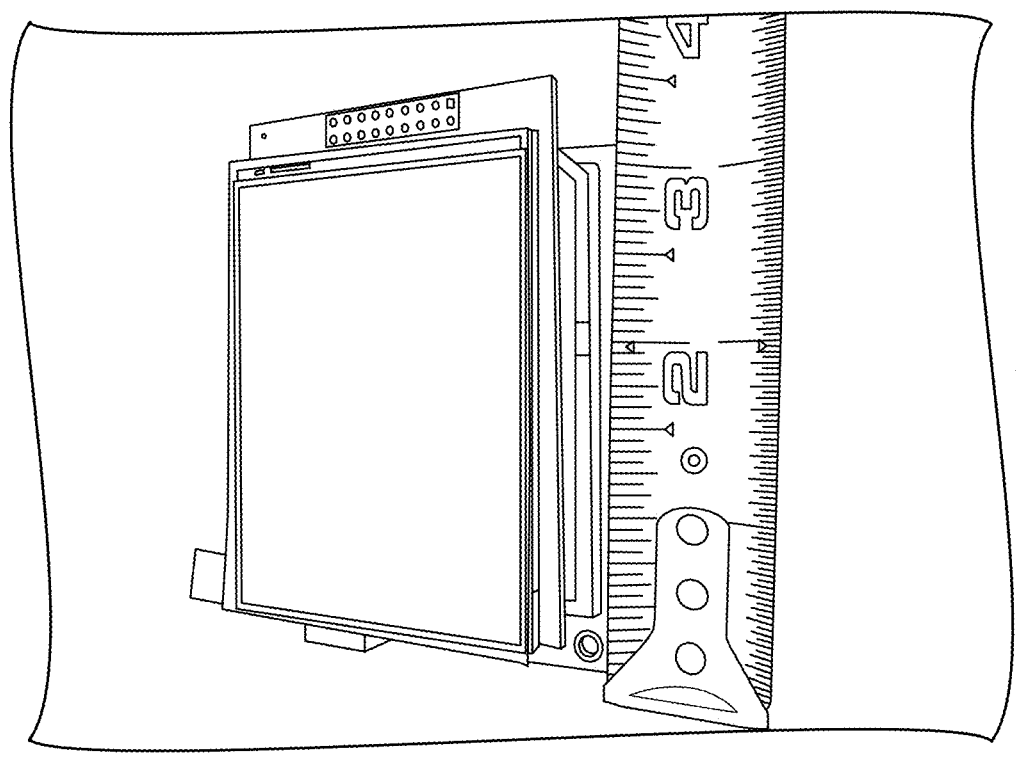
FIG. 6 is a photograph showing an Arduino Uno and a larger display screen.
Figure 5:
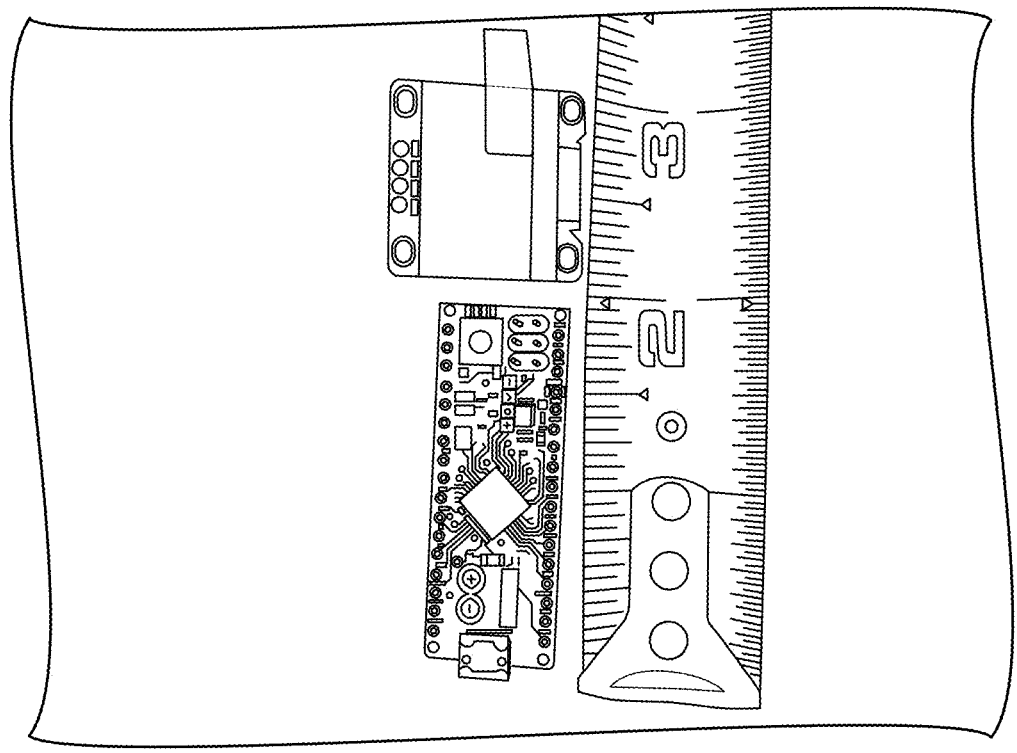
FIG. 5 is a photograph showing an Arduino micro and a display screen.

FIG. 5 shows an Arduino Micro having a smaller board, as well as a 1-inch screen. A 1-inch screen may not be able to display desired full range of parameters. FIG. 6 shows an Arduino Uno board, which is larger than the Micro, and which has been fitted with a larger 2.8-inch screen. A ruler is alongside for scale.

Arduino acts differently than Raspberry Pi in that it does not inherently have a way for the user to interact with the board other than adjusting the code that you upload to the board. Also, when a program is uploaded, it will automatically begin running once the Arduino board is powered. Hence, embodiments comprising Arduino microprocessors are useful for embodiments that require only turning on a switch. In order to use the device, the user powers the device on and the device will immediately begin collecting data and providing outputs. A display screen can be used to output the desired output. The display screen may be a touch screen.

Figure 4:
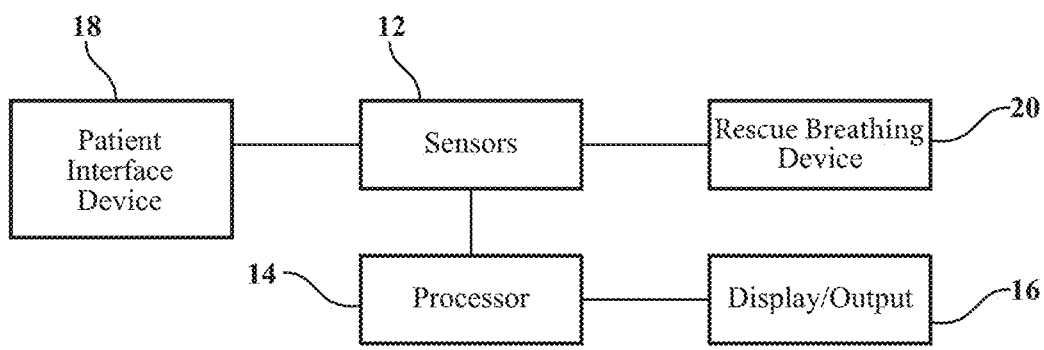
FIG. 4 is a block diagram showing an example of a ventilation system including a measuring and analysis system in accordance with an embodiment of the present invention.

To analyze a patient's breathing during rescue breathing, the fundamental clinical variables to be measured are identified as peak pressure, respiratory rate, volume provided each breath (tidal volume), and volume exhaled. These quantities can be extracted from two measureable variables: air flow rate (both inspiratory and expiratory) and pressure. Using an embodiment of the present device, as shown in FIG. 4, the sensors 12 are connected between the patient interface device 18 and the rescue breathing device 20. For example, the sensors are bidirectional air flow meter and pressure sensor. The air flow rate and pressure measured by the sensors are processed by a data acquisition system (i.e., the processor 14) and the processed variables of interest are displayed on a display/output 16, such as a screen. FIG. 2 gives an example of respiratory parameters displayed on the screen, including peak pressure, respiratory rate, volume exhaled, tidal volume, minute ventilation, compression rate, and CPR fraction, estimated by the processor based on the air flow rate and pressure.

Data Analysis

1. Measuring Bag-Valve Mask Seal and Rescue Breath Delivery

A self-inflating resuscitation bag with a facemask (bag-valve mask) is commonly used to provide rescue breaths for patients in cardiac arrest. Air leak around the mask and gastric insufflation (air going into the stomach instead of the lungs) will likely cause ineffective rescue breaths.

In an embodiment of the present invention, the measuring and analysis device is configured to measure seal quality of the bag-valve mask. The sensor device 22 measures airflow and pressure in two directions, i.e., from the resuscitation bag to the patient and vice versa. Based on the measurements of airflow and pressure, the measuring and analysis device determines the quality of the mask seal and the flow of air into the lungs. For example, a good mask seal produces a baseline pressure in the system that is greater than atmospheric pressure with the volume of air delivered to the lungs equal to the volume of air returning to the device. A poor mask seal produces an inconsistent baseline pressure, and the volume of air supposedly delivered to the lungs would not equal the volume of air returned. Gastric insufflation or an iatrogenic pneumothorax (air escaping from the lungs to the intrathoracic space) produces a constant baseline pressure with volumes of air delivered greater than the volume returned to the sensor.

2. Differentiating Rescue Breaths from Continuous Chest Compressions

Cardiopulmonary resuscitation (CPR) involves delivering rescue breaths to oxygenate the blood and chest compressions to circulate the blood. The presently disclosed device can be used to differentiate airflow due to rescue breaths from inadvertent airflow caused by physical compression of the thoracic cavity, which occurs continuously during cardiac arrest resuscitations.

In an embodiment of the present invention, the measuring and analysis device is configured to differentiate rescue breaths from chest compressions using the frequency and amplitude of changes in airflow and pressure. This allows for the accurate measurement of ventilation parameters such a tidal volume (milliliters per breath) and respiratory rate (breaths per minute).

Differentiation between the rescue breaths and chest compressions is made possible because they occur at very different frequencies. In order to identify these frequencies, Fast Fourier Transform, or FFT, may be implemented. FFT analyzes the raw voltage signal from the flow meter and identifies the presence of two regularly occurring fluctuations that are at different frequencies. The flow from the rescue breathing is at lower frequency (a fraction of less than 1 Hertz) and the flow from the chest compressions is at a higher frequency (1-2 Hertz). The output from the FFT is the amplitude of the fluctuations at each one of these two frequencies and is subsequently used to band-pass filter the raw signal at each one of these frequencies, obtaining two separate time traces of the applied breaths and the chest compressions. Based on the output, several important parameters can be determined and displayed, including the rates of breaths and chest compressions administered to the patient, the flow rate at each one of these components, the relative phase between them, their duty cycles, and the signal shape.

3. Synchronizing Rescue Breaths and Chest Compressions

American Heart Association Cardiac Arrest Guidelines recommend performing rescue breaths at a rate of 8 to 10 per minute and chest compressions at a rate of 100 to 120 per minute. There is significant debate on whether chest compressions should be briefly interrupted to administer rescue breaths when using a bag-valve mask. Guidelines recommend 30 compressions followed by 2 breaths when performing interrupted cardiopulmonary resuscitation. After an advanced airway is placed in the patient's throat (endotracheal tube or supraglottic airway), guidelines recommend performing continuous chest compressions and rescue breaths.

In an embodiment of the present invention, the measuring and analysis device of the present invention is configured to assess the synchronization between chest compressions and rescue breaths. The measuring and analysis device of the present invention is capable of detecting both chest compressions and rescue breaths, which enables synchronization of the two halves of cardiopulmonary resuscitation. By optimizing the timing, depth and duration of rescue breaths, the present device can ensure rescue breaths are delivered in a coordinated and efficacious manner that maximizes heart and lung function, regardless of whether an interrupted or continuous technique is followed. This enables a comprehensive second-by-second analysis of cardiopulmonary resuscitation.

4. Measuring Chest Compression Quality

In addition to the rate goals described above, guidelines recommend chest compressions be minimally interrupted with a compression fraction of 60-80% (time performing chest compressions divided by the total time), at a depth of 2 to 2.5 inches, and released 100% between compressions to allow full chest recoil.

The present device is capable of measuring chest compression rate and fraction using airflow and pressure. In addition, quality often declines after 2 minutes of high intensity work by treating clinicians. The present device may be configured to assess the relative depth of chest compressions, for example by measuring changes in the amplitude of the chest compression waveform. The present device is configured to measure both rescue breaths and chest compressions. This simplifies the logistics of a complex resuscitation, while still providing real-time feedback on resuscitation targets set by the American Heart Association.

5. Guiding Initial Settings for Mechanical Ventilation

The initial goal of clinical care for cardiac arrest patients is to achieve return of spontaneous circulation (return of native heart function). Post-arrest patients are often comatose and not breathing on their own. As such, these patients are placed on mechanical ventilators, once they are at a hospital. Mechanical ventilators cannot be used intra-arrest due to high peak airway pressures caused by chest compressions, and the bulk, weight, complexity, and cost of mechanical ventilators are prohibitive in the prehospital environment.

Initial settings for mechanical ventilation post-arrest are based on heuristics alone, which may result in re-arrest, and are often retained by the Intensive Care Unit hours after admission to the hospital. Arterial blood gas analysis can take up to an hour or more to result and does not directly inform ventilator settings.

In one embodiment, the present device is configured to measure the ventilation parameters needed to set a mechanical ventilator. The physiologic data collected by the present device intra-arrest, including respiratory rate (breaths per minute), tidal volume (milliliters per breath), minute ventilation (liters per minute), volume exhaled (milliliters per breath), peak pressure (highest pressure during a breath), positive-end expiratory pressure (pressure between breaths), and graphs of pressure and volume over time including pressure-volume loops, among others, can be used to inform and optimize ongoing ventilation in the post-arrest period.

6. Current and Novel American Heart Association Guidelines

American Heart Association Cardiac Arrest Guidelines recommend rescue breaths be delivered at a rate of 8 to 10 per minute, with each breath delivered over 1 second, and a tidal volume that produces minimal chest rise.

In an embodiment of the present invention, the measuring and analysis device is configured to determine the metrics including delivery rate of the rescue breaths, the duration of the rescue breaths, tidal volume, thereby providing real-time feedback to clinicians on how closely they are adhering to guidelines, both in clinical practice and in training simulations. These metrics can also be combined to produce an overall measure of "high-quality rescue breathing" that is reported to the clinician along with specific feedback on how to improve via light, sound, and/or tactile feedback. In addition, based on the measurements of any desired ventilation parameter, novel respiratory metrics can be discovered that are associated with survival and the creation of new cardiac arrest guidelines may be spurred. For example, a low tidal volume strategy of 6 mL per kg of ideal body weight has been shown to improve survival for patients with acute respiratory distress syndrome, and may be a reasonable target for cardiac arrest.

Core Architecture

The processor of the present device is configured to fulfill the following steps:

Take in an analog voltage signal from a mass flow meter
Remove random noise (smoothing) improve signal/noise ratio
Scale the voltage to mass flow rate (L/min)
Identify air delivery start and stop
Identify exhale start and stop
Calculate delivery volumes
Calculate exhalation volumes
Calculate a moving average respiratory frequency
Calculate a multiple breath average of volume delivered (i.e. minute ventilation)
Take in analog voltage signal from pressure sensor
Scale voltage to pressure (cmH20)

Figure 7:
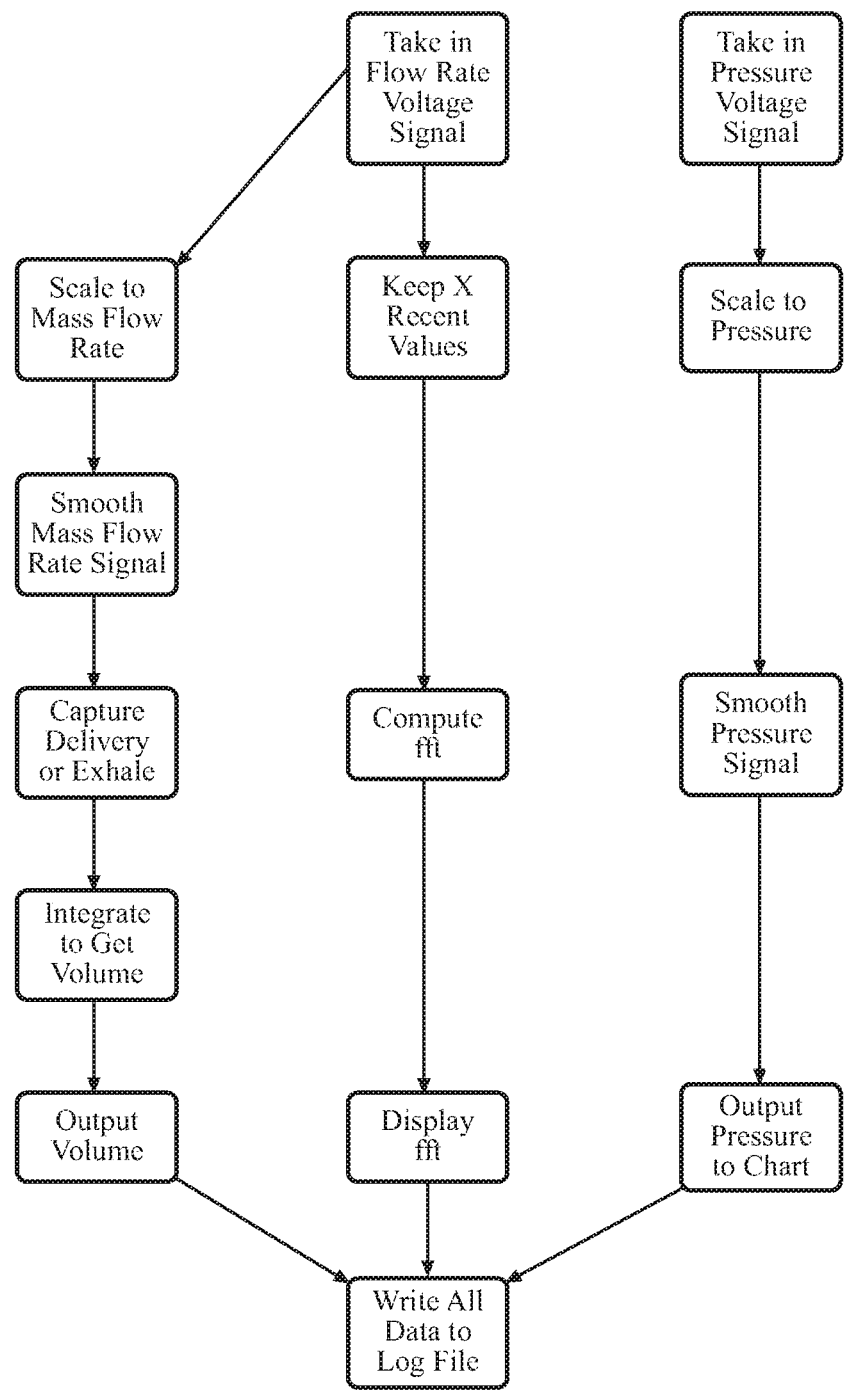
FIG. 7 is a flow diagram showing the algorithm flow in accordance with an embodiment of the present invention.

An example of a flow diagram of these steps is shown in FIG. 7. Based on the mass flow rate and pressure, clinical variables such as peak pressure, respiratory rate, volume exhaled and tidal volume can be determined. Additional clinical variables such as minute ventilation, compression rate, and CPR fraction can also be calculated.

Figure 8:
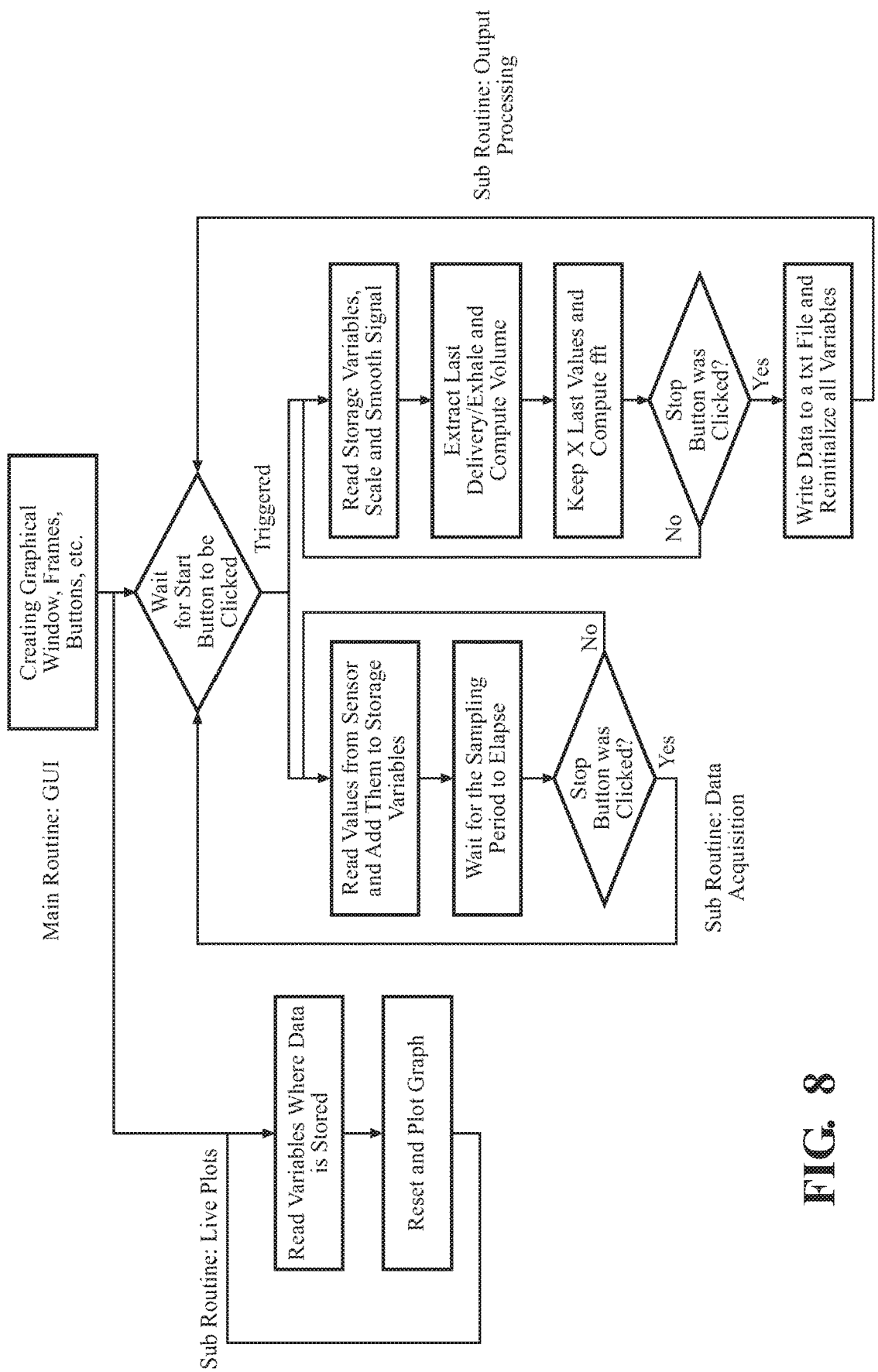
FIG. 8 is a flow diagram showing the triple-threaded algorithm flow in accordance with an embodiment of the present invention.

In one embodiment, the processor is configured to provide real-time plots. The structure of this algorithm adds a real-time plotting routine in the main loop, alongside the data acquisitions and processing tasks that are split into two parallel subroutines. Three routines are executed in parallel for this particular version of the code. An example of a flow diagram for this architecture is shown in FIG. 8. A basic integration algorithm is used to compute the volume delivered and exhaled. This integration is based on the rectangle rule. Further enhancement may be made to increase integration accuracy. The next function is a smoothing function, for which a moving-average method was selected to reduce signal noise. Using a real time Fast Fourier Transform, the code is also able to detect respiratory rates in both real time and a user set moving average. In addition to respiratory rates, this FFT allows the differentiation between chest compressions and respiratory rates using a signal filtering technique known as band pass filtering. The last main function called in the main script is a trigger function for detecting the last delivery or the last exhale of air through the measuring and analysis device. To detect the last delivery or the last exhale of air through the measuring and analysis device, the function scans the data in real time. Once it has detected a value above a user set threshold, it adds that time stamp to a new list and scans in real time until a value is found to be below the threshold. The data points between these two points in time is then integrated to obtain the volume delivered or exhaled. The threshold may be defined as user-input so as to ensure detection of deliveries and exhalations. The threshold may also be set by the code based on prior test results. The data from data acquisition is also written to text files in memory for export and further analysis after use.

Note that the algorithms described in FIGS. 7 and 8 are not meant to be limiting and are merely examples used to describe the function of the present device. What is described can also be achieved by different algorithms.

As will be clear to those of skill in the art, the embodiments of the present invention illustrated and discussed herein may be altered in various ways without departing from the scope or teaching of the present invention. Also, elements and aspects of one embodiment may be combined with elements and aspects of another embodiment. It is the following claims, including all equivalents, which define the scope of the invention.

The invention claimed is:

1. A ventilation system for ventilation of a patient, comprising:
   a patient interface device for attaching to the patient; and
   a measuring and analysis device for measuring and analyzing breathing of the patient, the measuring and analysis device comprising:
      a connector housing defining a passage, a first portion of the connector housing connected to the patient interface device;
      a bidirectional air flow sensor disposed in the connector housing for measuring an air flow rate through the connector housing;
      a bidirectional pressure sensor disposed in the connector housing for measuring a pressure in the connector housing;
      a processor configured for data acquisition, data storage, data processing, and data output based on the air flow rate and the pressure; and
      an output device configured to output the data output, wherein the processor is configured to analyze signals from the air flow sensor and/or the pressure sensor to differentiate rescue breaths administered to the patient from the chest compressions administered to the patient by:
      (i) performing Fast Fourier Transform (FFT) on signals from the air flow sensor and/or the pressure sensor to identify a first frequency corresponding to the rescue breaths and a second frequency corresponding to the chest compressions; and
      (ii) band-pass filtering the signals from the air flow sensor and/or the pressure sensor at each of the first and second frequencies to obtain a separate time trace for each of the rescue breaths and the chest compressions; and
   a manual breath delivery device for delivering the rescue breaths to the patient, the manual breath delivery device connected to a second portion of the connector housing.

2. The ventilation system according to claim 1, wherein the patient interface device is a face mask, and the manual breath delivery device is a self-inflating bag.

3. The ventilation system according to claim 2, wherein the measuring and analysis device is operable to evaluate respiratory parameters based on the air flow rate and the pressure, wherein the respiratory parameters are selected from the group consisting of baseline pressure, peak pressure, tidal volume, and exhalation volume, respiratory rates, minute ventilation, chest compression rates, chest compression depths, and chest compression fractions.

4. The ventilation system according to claim 3, wherein the measuring and analysis device is operable to determine airway blockage and other abnormalities of rescue breaths based on the baseline pressure, tidal, and exhalation volumes.

5. The ventilation system according to claim 3, wherein the measuring and analysis device is operable to determine a seal quality of the patient interface device based on the baseline pressure, tidal and exhalation volumes.

6. The ventilation system according to claim 3, wherein the measuring and analysis device is operable to determine a quality of chest compressions based on the chest compression rates, chest compression depths, and chest compression fractions.

7. The ventilation system according to claim 1, wherein the output device is a display attached to the processor for displaying the data output.

8. The ventilation system according to claim 7, wherein the display is integrated into a monitor.

9. The ventilation system according to claim 1, wherein the processor is configured to time-stamp events for post-event analysis.

10. The ventilation system according to claim 1, further comprising one or more inline ports for suction, medications, or end-tidal $CO_2$.

11. The ventilation system according to claim 1, wherein the ventilation system is used during cardiac arrest resuscitations.

12. The ventilation system according to claim 1, wherein the measuring and analysis device is operable to enable synchronization between the rescue breaths and chest compressions by adjusting a timing, depth, and duration of the rescue breaths based on the time traces such that the rescue breaths are delivered in a coordinated manner with the chest compressions.

13. The ventilation system according to claim 1, wherein the patient interface device is a mouth piece for a face mask, a supraglottic airway, an endotracheal tube, a tracheostomy tube, or other device used to deliver a rescue breath.

14. The ventilation system according to claim 1, wherein the measuring and analysis device is disposable.

15. The ventilation system of claim 1, further comprising a filter or trap for filtering respiratory secretions over the air flow sensor and the pressure sensor.

16. The ventilation system of claim 1, wherein the processor is built into the measuring and analysis device.

17. The ventilation system of claim 1, wherein the air flow sensor and the pressure sensor communicate with the processor via a wireless connection.

18. The ventilation system according to claim 1, wherein the ventilation system is operable with real-time feedback based on data output from the processor.

19. A measuring and analysis device for measuring and analyzing breathing of a patient, the measuring and analysis device comprising:
   a connector housing defining a passage, a first portion of the connector housing connected to a patient interface device;
   a bidirectional air flow sensor disposed in the connector housing for measuring an air flow rate through the connector housing;
   a bidirectional pressure sensor disposed in the connector housing for measuring a pressure in the connector housing; and
   a processor configured for data acquisition, data storage, data processing, and data output based on the air flow rate and the pressure, wherein the processor processes signals from the air flow sensor and/or the pressure sensor to differentiate rescue breaths administered to the patient from the chest compressions administered to the patient by:

(i) performing Fast Fourier Transform (FFT) on signals from the air flow sensor and/or the pressure sensor to identify a first frequency corresponding to the rescue breaths and a second frequency corresponding to the chest compressions; and
(ii) band-pass filtering the signals from the air flow sensor and/or the pressure sensor at each of the first and second frequencies to obtain a separate time trace for each of the rescue breaths and the chest compressions, whereby the ventilation system is operable with real-time feedback based on data output from the processor.

20. The measuring and analysis device according to claim 19, further comprising a display attached to the processor for displaying the data output.

21. A method of administering cardiopulmonary resuscitation (CPR), the method comprising the steps of:
providing a manual ventilation device having a manual breath delivery device, a patient interface device, and a measuring and analysis device, the measuring and analysis device comprising:
a connector housing for connecting between the flexible self-inflating air chamber and the mouthpiece, the connector housing defining a passage;
a bidirectional air flow sensor disposed in the connector housing for measuring an air flow rate through the flexible self-inflating air chamber;
a bidirectional pressure sensor disposed in the connector housing for measuring a pressure in the connector housing;
a processor for data acquisition, data storage, and calculation of respiratory parameters based on the air flow rate and the pressure; and
an output attached to the computer for providing real-time feedback;
measuring the air flow rate and the pressure using the air flow sensor and pressure sensor;
evaluating respiratory parameters based on the air flow rate and the pressure, wherein the respiratory parameters are selected from the group consisting of baseline pressure, peak pressure, tidal volume, and exhalation volume, respiratory rates, minute ventilation, chest compression rates, chest compression depths, and chest compression fractions;
performing Fast Fourier Transform (FFT) on signals from the air flow sensor and/or the pressure sensor to identify a first frequency corresponding to rescue breaths and a second frequency corresponding to chest compressions;
band-pass filtering the signals from the air flow sensor and/or the pressure sensor at each of the first and second frequencies to obtain a separate time trace for each of the rescue breaths and the chest compressions, thereby differentiating rescue breaths from chest compressions; and
outputting the respiratory parameters as output signals on the output.

22. The method according to claim 21, wherein the output signals are visual, audio, or tactile.

23. The method according to claim 21, further comprising synchronizing the rescue breaths and the chest compressions by optimizing the timing, depth and duration of the rescue breaths to ensure the rescue breaths are delivered in a coordinated manner with the chest compressions that maximizes heart and lung function, regardless of whether an interrupted or continuous chest compression technique is used.

24. The method according to claim 21, further comprising using the respiratory parameters for guiding ventilator settings.

25. The method according to claim 21, wherein the outputting includes display of respiratory waveforms.

* * * * *